(12) United States Patent  (10) Patent No.: US 8,758,426 B2
Hood et al.  (45) Date of Patent: Jun. 24, 2014

(54) TUBULAR GRAFT

(75) Inventors: Robert Gordon Hood, Longforgan Tayside (GB); Craig McLeod Duff, Tayside (GB)

(73) Assignee: Vascular Flow Technologies Limited (GB)

( * ) Notice: Subject to any disclaimer, the term of this patent is extended or adjusted under 35 U.S.C. 154(b) by 1347 days.

(21) Appl. No.: 11/470,007

(22) Filed: Sep. 5, 2006

(65) Prior Publication Data

US 2007/0129783 A1 Jun. 7, 2007

(30) Foreign Application Priority Data

Sep. 6, 2005 (GB) .................................. 0518126.8

(51) Int. Cl.
*A61F 2/82* (2013.01)
(52) U.S. Cl.
USPC .................... 623/1.13; 623/1.22; 623/1.32
(58) Field of Classification Search
USPC ............... 623/1.13, 1.22, 1.23, 1.37
See application file for complete search history.

(56) References Cited

U.S. PATENT DOCUMENTS

| 4,503,568 | A | | 3/1985 | Madras | |
| 4,629,458 | A | * | 12/1986 | Pinchuk | 623/1.47 |
| 4,990,143 | A | | 2/1991 | Sheridan | |
| 5,104,402 | A | | 4/1992 | Melbin | |
| 5,127,919 | A | * | 7/1992 | Ibrahim et al. | 623/1.51 |
| 6,494,904 | B1 | * | 12/2002 | Love | 623/1.1 |
| 2002/0165598 | A1 | * | 11/2002 | Wahr et al. | 623/1.11 |
| 2002/0179166 | A1 | * | 12/2002 | Houston et al. | 138/39 |
| 2003/0023299 | A1 | | 1/2003 | Amplatz et al. | |
| 2003/0225453 | A1 | * | 12/2003 | Murch | 623/1.21 |

FOREIGN PATENT DOCUMENTS

| WO | 0038591 | A2 | 7/2000 |
| WO | 0189419 | A1 | 11/2001 |
| WO | 03103540 | A1 | 12/2003 |
| WO | 2004047908 | A2 | 6/2004 |
| WO | 2005092240 | A1 | 10/2005 |

* cited by examiner

*Primary Examiner* — Thomas J Sweet
*Assistant Examiner* — Rebecca Preston
(74) *Attorney, Agent, or Firm* — Kaplan Breyer Schwarz & Ottesen, LLP

(57) ABSTRACT

A tubular graft comprising an internal helical formation which imparts helical flow on fluid passing through the tubular graft. One end of the tubular graft is tapered from an inner base to an outer tip.

10 Claims, 16 Drawing Sheets

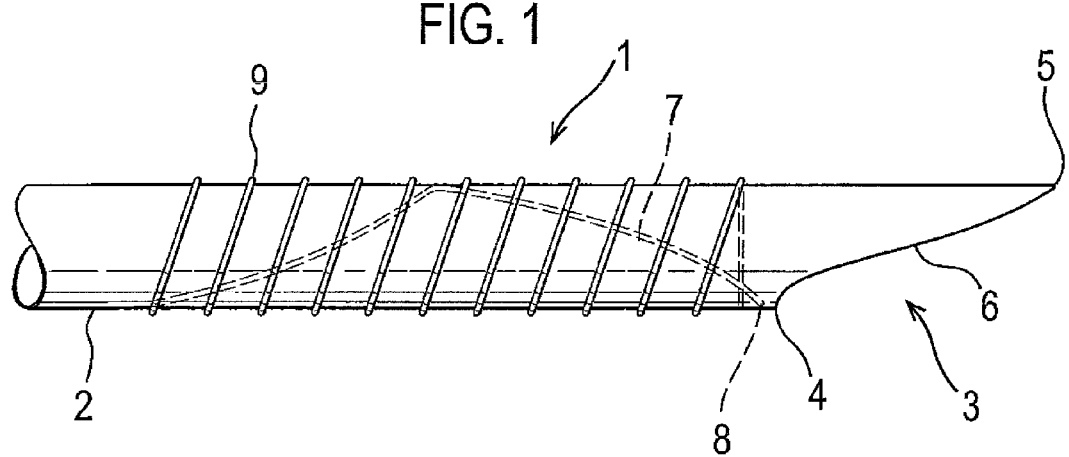
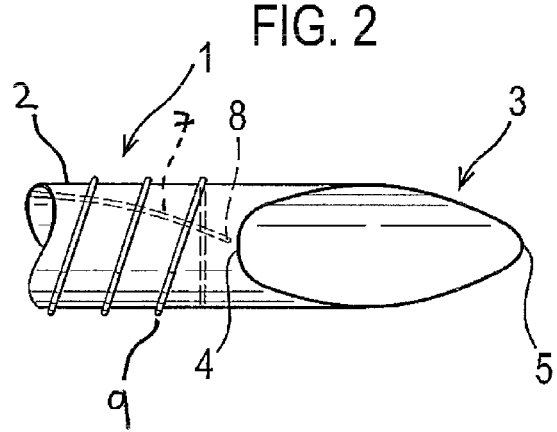

sheep 1   2003/11/20 sheep 2   2003/11/20

FIG. 22
FIG. 23
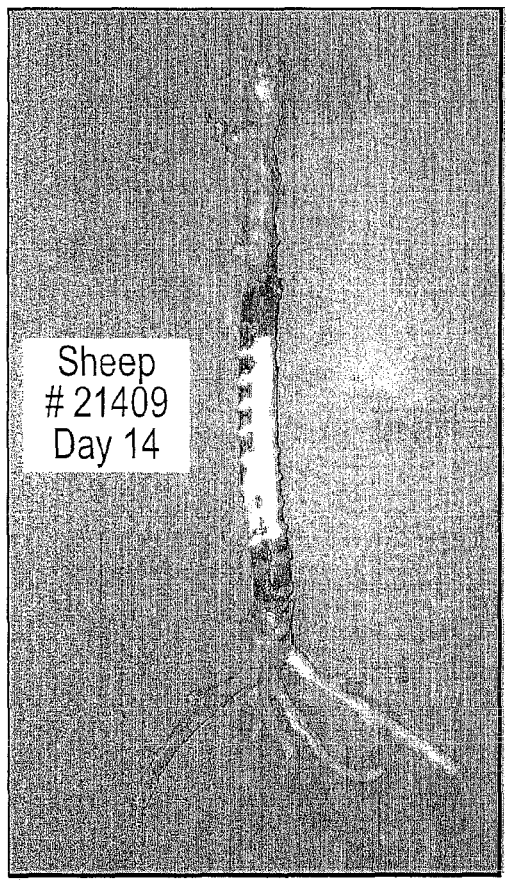
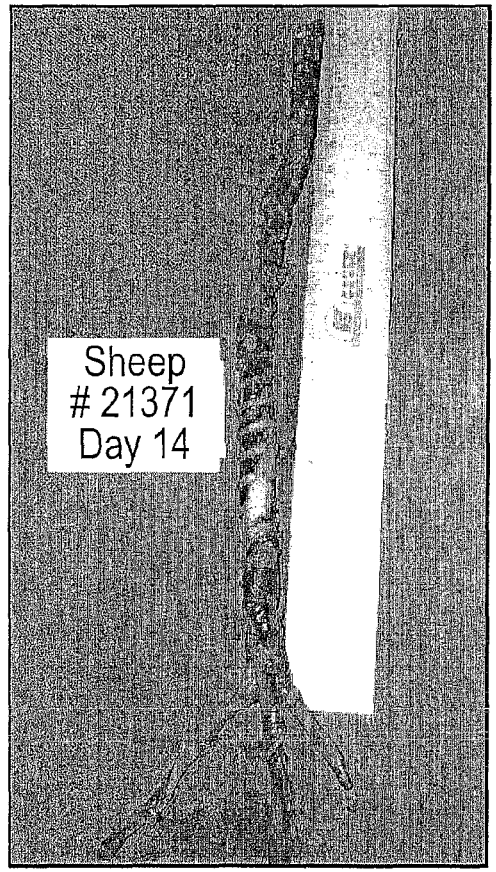

TUBULAR GRAFT

The present invention relates to a tubular graft and, more particularly, a tubular graft comprising an internal helical formation capable of imparting a helical flow on fluid passing through the graft. The present invention also relates to a method of implanting such a tubular graft.

In the fields of medicine and pathology, it has been observed that certain individuals acquire damage to tubular organs, especially blood vessels. One treatment for such conditions is to perform an anastomosis to replace a section of the tubular organ with an artificial tubular graft. In the procedure, the artificial tubular graft is sutured into position between healthy sections of the organ, at either end of the damaged section, and replaces the damaged section.

WO 00/38591 discloses a particular type of artificial graft which comprises means, such as internal ridging and/or grooving, for imparting helical flow on the fluid, such as blood, passing through the graft. The advantage of imparting such flow is that it eliminates or reduces turbulence in the fluid. This is particularly advantageous when the graft is carrying blood because it has been observed that turbulent blood flow can be a cause of atherosclerosis.

When artificial tubular grafts of this type are being implanted, so as to replace, for example, a diseased section of a blood vessel, the surgeon forms an aperture in a healthy section of the blood vessel, at one end of the diseased section. The surgeon then locates one end of the vascular graft over the aperture and sutures it into place. The same steps are taken in another healthy section of blood vessel, at the opposite end of the diseased section, so that the tubular graft bypasses the diseased section of blood vessel.

The present invention arises from the finding that by shaping one or both of the ends of the tubular graft, it is easier for the surgeon to carry out the surgery. In particular, it is easier for the surgeon to suture the tubular graft in place.

According to one aspect of the present invention, there is provided a tubular graft comprising an internal helical formation for imparting a helical flow on fluid passing through the tubular graft, wherein one end of the tubular graft is tapered from an inner base to an outer tip. Conveniently, said one end of the tubular graft is tapered sinusoidally such that the end forms an egg-shaped orifice, the radius of curvature at the outer tip being smaller than the radius of curvature at the inner base. Preferably, the internal helical formation terminates at said one end within 180° of the inner base, more preferably within 120° of the inner base and even more preferably within 60° of the inner base. Advantageously, the internal helical formation terminates at said one end at the inner base. Conveniently, the helix angle of the internal helical formation is between 8° and 20°. Preferably, the internal helical formation is a ridge which extends inwardly from the internal surface of the tubular graft. Advantageously, the tubular graft comprises an external helical formation for supporting the tubular graft. Conveniently, the external helical formation has a helix angle greater than 50° and preferably between 65° and 80°. Preferably, the other end of the tubular graft is tapered in the same way as said one end.

According to another aspect of the present invention there is provided a method of performing an anastomosis between a tubular graft as described above and a tubular organ of a patient comprising the steps of:
(a) forming an aperture in the tubular organ, the aperture having a shape corresponding to the shape of the orifice formed by said one end of the tubular graft;
(b) locating said one end of the tubular graft so that it is aligned with said aperture; and
(c) securing the tubular graft to the tubular organ such that said one end of the tubular graft remains in position relative to said aperture.

Conveniently, the method further comprises the steps of:
(d) forming a second aperture in the tubular organ, the second aperture having a shape corresponding to the shape of the orifice formed by said other end of the tubular graft,
(e) locating said other end of the tubular graft so that it is aligned with said second aperture; and
(f) securing the tubular graft to the tubular organ such that said other end of the tubular graft remains in position relative to said second aperture.

The terms "helix" and "helical" are used herein to cover the mathematical definitions of helix and helical and combination of mathematical definitions of helical and spiral.

In order that the present invention may be more readily understood, and so that further features thereof may be appreciated, embodiments of the invention will now be described, by way of example, with reference to the accompanying drawings in which:

FIG. 1 is a side view of a portion of a tubular graft in accordance with one embodiment of the present invention;

FIG. 2 is a view from below of a portion of the tubular graft shown in FIG. 1;

FIG. 22 is a photograph of the explanted graft of the first sheep, 14 days post implantation;

FIG. 23 is a photograph of the explanted graft of the second sheep, 14 days post implantation;

Figure 3:
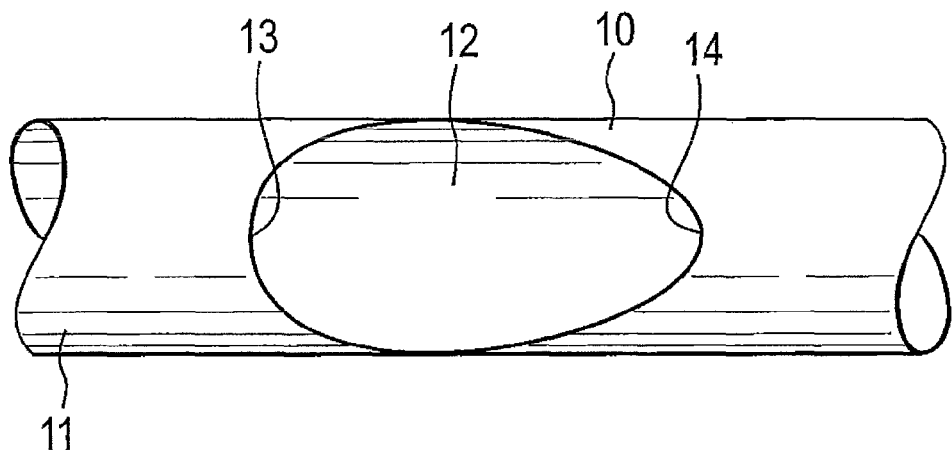
FIG. 3 is a top view of a section of a blood vessel prepared in accordance with one embodiment of the present invention.

Referring to FIGS. 1 and 2, a tubular graft 1, comprises a tubular section 2 which has a first tapered end 3. The first end 3 is tapered from an inner base 4 to an outer tip 5 such that the outer tip 5 extends outwardly from the main tubular body 2 further than the base 4 and thus the outer tip 5 forms a flap which overhangs the base 4. Furthermore, when viewed from the side, as shown in FIG. 1, the taper from the base 4 to the tip 5 is approximately sinusoidal, curving from a relatively sharp point tip 5, through a relatively straight, diagonal section 6 to a significant curve, which becomes almost perpendicular with the longitudinal axis of the tubular section 2, at the base 4. This has the effect that, when the tubular graft 1 is viewed from below, as shown in FIG. 2, the orifice that forms the end 3 is "egg-shaped". That is to say, the orifice is approximately elliptic but has a curved end at the base 4 with a relatively large radius of curvature (i.e. blunt end) and a curved end at the tip 5 with a relatively small radius of curvature (i.e. a sharp end).

The second end (not shown) of the tubular graft 1 is also tapered in the same way as the first end 3.

The tubular graft 1 is also provided with an internal helical ridge 7, which winds around the interior surface of the tubular graft, protruding inwardly therefrom. The internal helical ridge 7 has a helix angle of between 8° and 20° with the longitudinal axis of the tubular graft. The internal helical ridge 7 is thus capable of imparting helical flow to fluid, in particular blood, that passes through the tubular graft 1. The internal helical ridge 7 is located within the tubular graft 1 such that it terminates at its first end 8 at the base 4 of the first end 3 of the tubular graft 1.

Similarly, the second end (not shown) of the internal helical ridge 7 terminates at the base of the second end of the tubular graft 1.

In some embodiments the internal helical ridge is formed by a deformation helix formed on the exterior of the tubular section 2 which presses through the material of the tubular section into the interior of the tubular graft 1.

Around the exterior of the tubular section 2 is provided a support helix 9. The support helix 9 extends only around the tubular section 2 of the tubular graft 1 and does not extend onto the flap formed by the outer tip 5 overhanging the base 4. The tubular section 2 is made from a relatively flexible material such as ePTFE whereas the support helix 9 is made from a relatively rigid material such as polyurethane bonded or fused to the tubular section 2. The support helix 9 has a helical angle of greater than 50°, preferably between 65° and 80°. The support helix 9 maintains the shape of the tubular graft 1, allowing it to flex but greatly reducing the risk of a kink forming.

Figure 4:
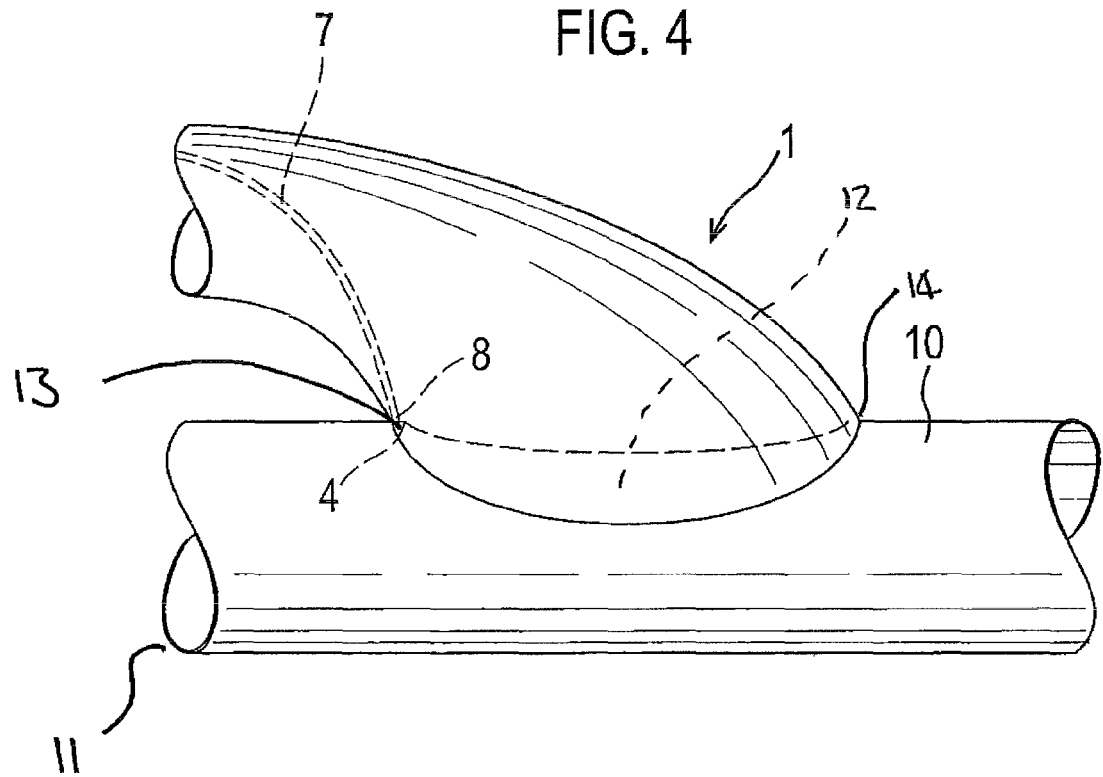
FIG. 4 is a side view of the section of blood vessel shown in FIG. 3 with a portion of a tubular graft according to a further embodiment of the present invention sutured in place.

Referring to FIGS. 3 and 4, the use of the tubular graft 1 not shown in FIG. 3) in an anastomosis procedure to replace a damaged section of a blood vessel will now be described. In order to implant the tubular graft 1, a healthy section of blood vessel 10 is selected adjacent to the damaged section of blood vessel 11. An aperture 12 is formed in the healthy section of blood vessel 10. The aperture 12 is "egg-shaped" being approximately elliptic having a base 13 which is curved with a relatively large radius of curvature and a tip 14 which is curved with a relatively small radius of curvature. Thus the aperture 12 is shaped to correspond to the shape of the orifice that forms the first end 3 not shown in FIGS. 3 and 4) of the tubular graft 1. The aperture 12 is sized to be slightly smaller than the orifice which forms the first end 3.

In the next step of the procedure, the first end 3 of the tubular graft 1 is located over the aperture 12 of the healthy section of blood vessel 10. The surgeon then sutures the tubular graft 1 to the healthy section of blood vessel 10, joining the edge of the first end 3 with the edge of the aperture 12. The egg-shape of the first end 3 of the tubular graft 1 provides the surgeon with the maximum amount of material in order to carry out the suturing step which assists the surgeon in performing the procedure. It is particularly helpful for the surgeon to have this additional material when suturing around the base 4 not shown in FIG. 3) of the first end 3 of the tubular graft 1.

The steps of forming an aperture are repeated in a second section of healthy blood vessel (not shown) at the other end of the damaged section of blood vessel 11. Similarly, the step of suturing the second end of the tubular graft 1 to the second section of healthy blood vessel over the second aperture is performed just as for the first end 3.

While the procedure is taking place, any blood is prevented from passing through the blood vessel being operated on but once the suturing of the tubular graft 1 to the blood vessel is complete, blood is allowed to pass through the blood vessel and into the tubular graft 1. The damaged section of blood vessel 11 is usually occluded and totally incorporated into the surrounding tissue, but occasionally it is removed.

It is to be appreciated that the location of the first end 8 not shown in FIG. 3) of the internal helical ridge 7 (not shown in FIG. 3) at the base 4 of the first end 3 of the tubular graft 1 provides improved flow of blood from the blood vessel to the tubular graft 1 and vice versa. This occurs because the helical ridge 7 imparts spiral flow on the blood flowing through the tubular graft 1 and this reduces turbulence through the junction between the tubular graft and the blood vessel, minimising cell damage and plaque build up.

While in the above described embodiment the first and second ends of the tubular graft 1 have the internal helical ridge 7 terminating at the base 4 of the respective ends, it is to be appreciated that in practice it is the blood flow through the distal (lower) anastomosis where blood flow disturbance creates vessel and cell damage. Thus it is most important that the end of the tubular graft 1 that forms the distal anastomosis has this location of the helical ridge 7.

Figure 5:
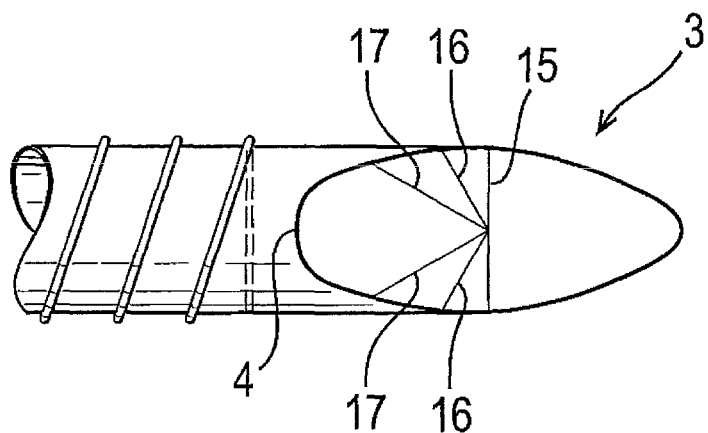
FIG. 5 is a view from below of a portion of a tubular graft showing the positioning of certain components in various alternative embodiments.
Figure 6:
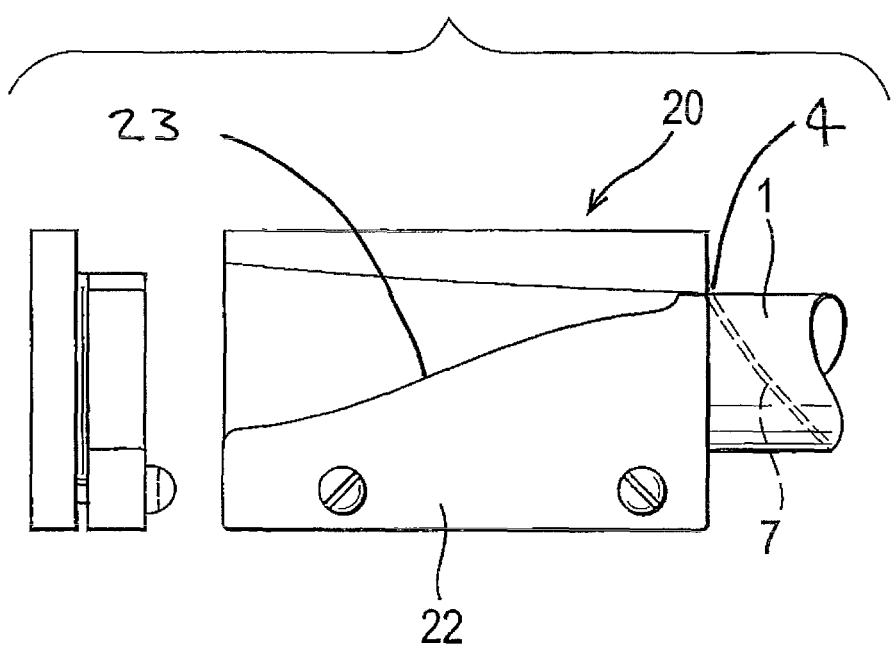
FIG. 6 is a schematic side view of a tubular graft according to a further embodiment of the present invention being formed.
Figure 7:
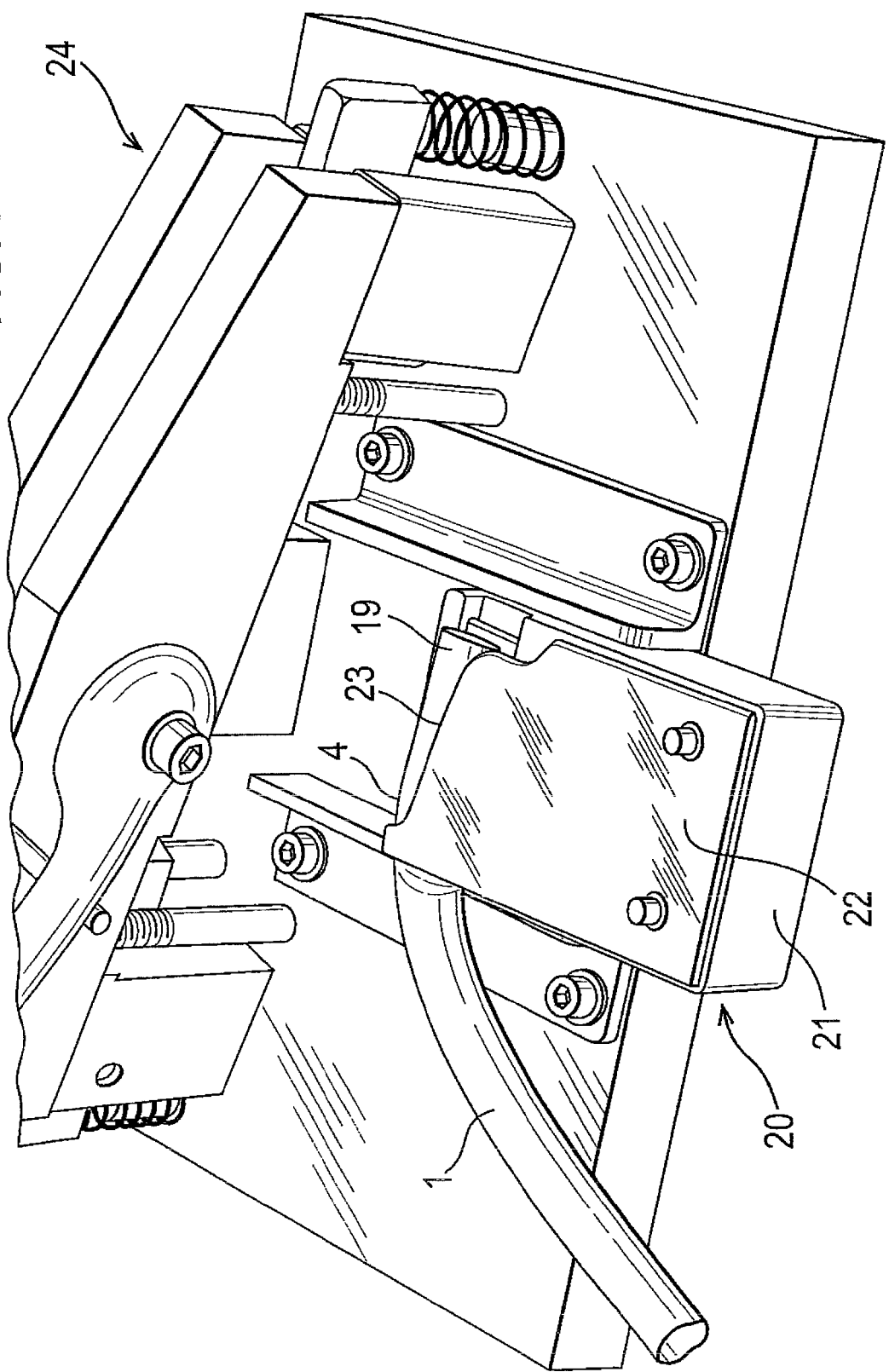
FIG. 7 is a photograph of a tubular graft according to another embodiment of the present invention positioned in a cutting press, for formation.

It is to be understood that, although it is preferred, it is not essential to the invention that the first end 8 of the internal helical ridge 7 be located exactly at the base 4 of the first end 3. Referring to FIG. 5, some alternative embodiments, the first end 8 not shown in FIG. 5) of the internal helical ridge 7 not shown in FIG. 5) is instead located within the arc defined by the 180° line 15 relative to the base 4 of the first end 3. In some alternative embodiments, the first end 8 of the internal helical ridge 7 is located within the arc within 120° of the base 4 as shown by the lines 16. In some further embodiments, the first end 8 of the internal helical ridge 7 is located within the arc within 60° line of the base 4 as shown by the lines 17.

Referring now to FIGS. 6 to 12, the preparation of a tubular graft 1 according to one embodiment of the present application will now be described.

A tubular graft 1 is provided having an orthogonally cut end 19 not shown in FIGS. 6 and 8-10). The tubular graft 1 has an internal helical ridge 7 not shown in FIGS. 7-12) which is shown schematically in FIG. 6. Up to this stage, the tubular graft 1 is formed as is known in the art such as that disclosed in WO00/38591.

Figure 11:
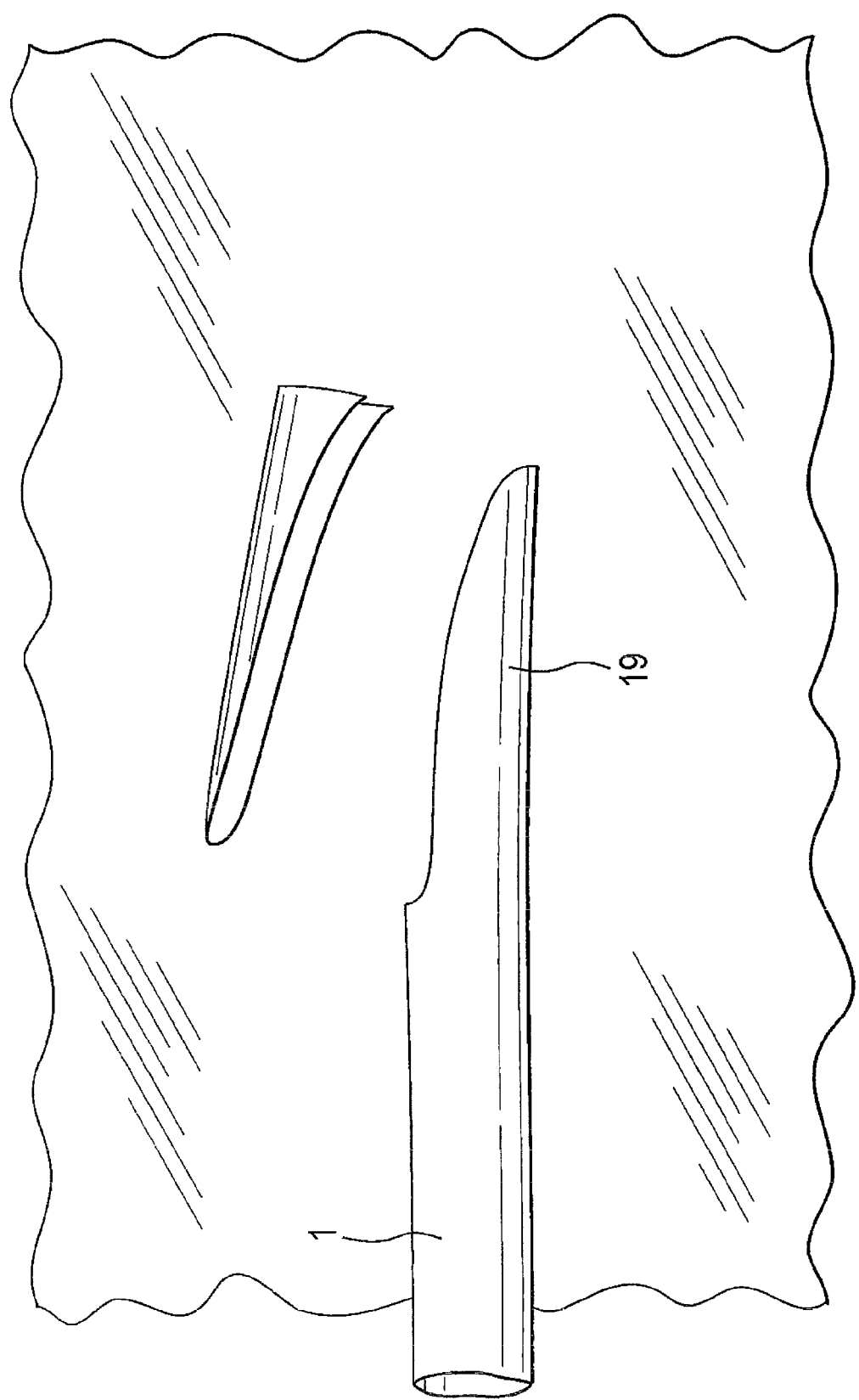
FIG. 11 is a view from the side of a tubular graft according to one embodiment of the present invention after one end has been formed.
Figure 12:
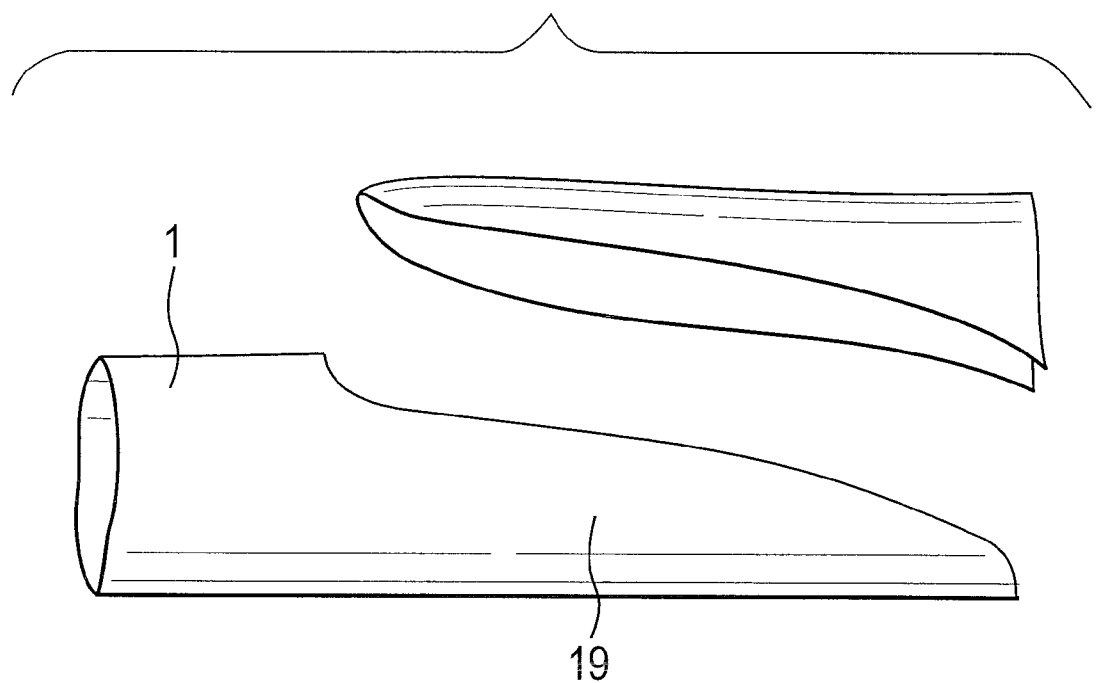
FIG. 12 shows a view from the side of a tubular graft according to a further embodiment of the present invention with one end formed.

The tubular graft 1 is then located on a high density polyurethane cutting block 20 (not shown in FIGS. 9-12) having a base 21 not shown in FIGS. 6 and 9-12) on which the end 19 of the tubular graft 1 is placed and over which a profiled metal template 22 not shown in FIGS. 11 and 12) is laid. The profiled metal template 22 has an end 23 not shown in FIGS. 8, 11 and 12) of sinusoidal shape corresponding to the desired cross-section of the first end of the tubular graft. The profiled metal template 22 is thus laid partly over the end 19 of the tubular graft 1 so as to define the shape of the end 19 which is to be cut. Subsequently, the tubular graft is rotated so that the internal helical ridge 7 lies at the part of the profiled metal template 22 which will form the base 4 knot shown in FIGS. 8-12) of the end 19 of the tubular graft. The profiled metal template 22 is then clamped down on the tubular graft 1 in order to hold it securely in place.

The tubular graft 1, together with the cutting block 20 and the profiled metal template 22 is then located under a press 24 having a blade (not shown) having the same shape as the shaped end 23 of the profiled metal template 22.

Figure 8:
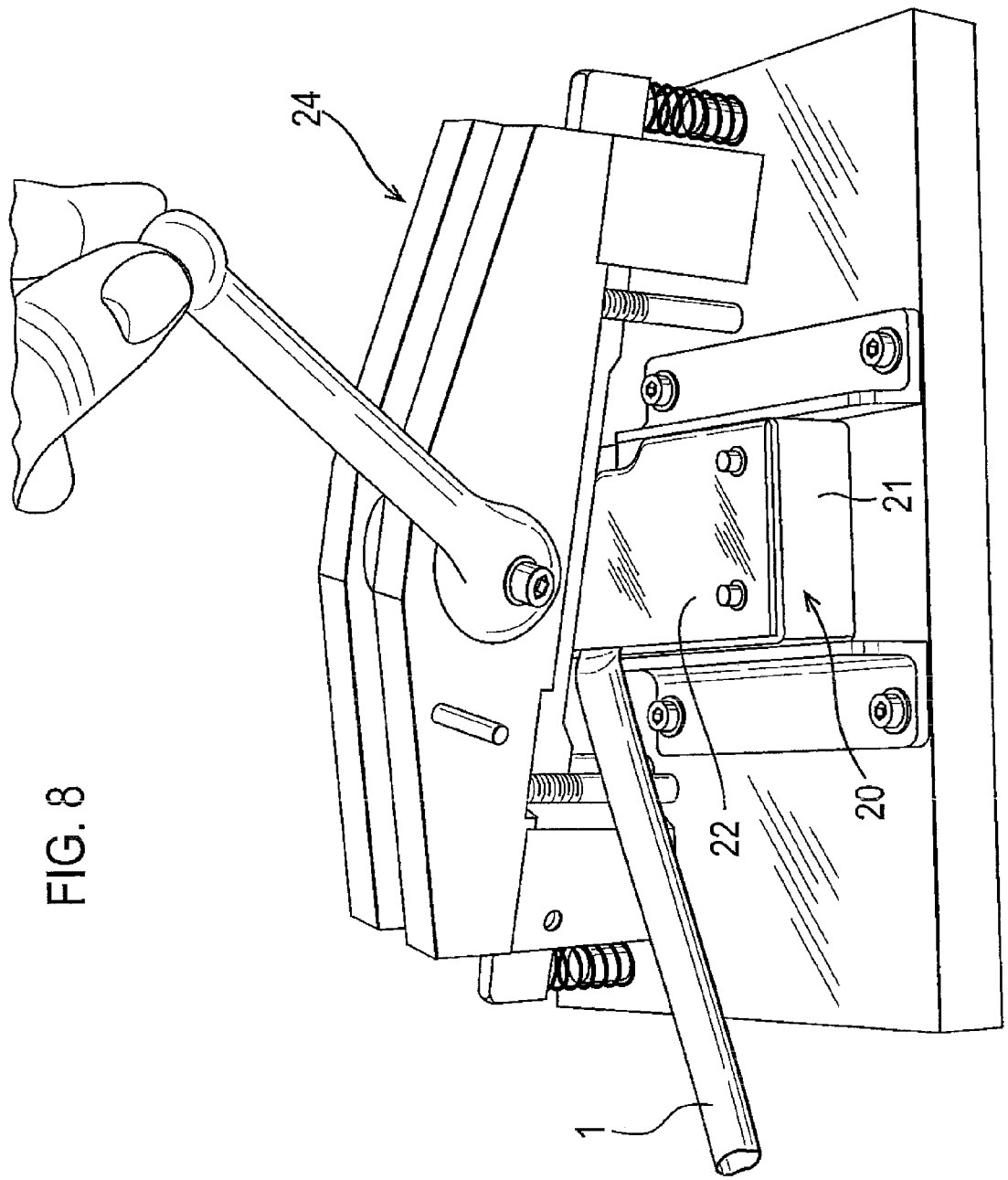
FIG. 8 is a photograph of the embodiment shown in FIG. 7, with cutting of the graft in progress.
Figure 9:
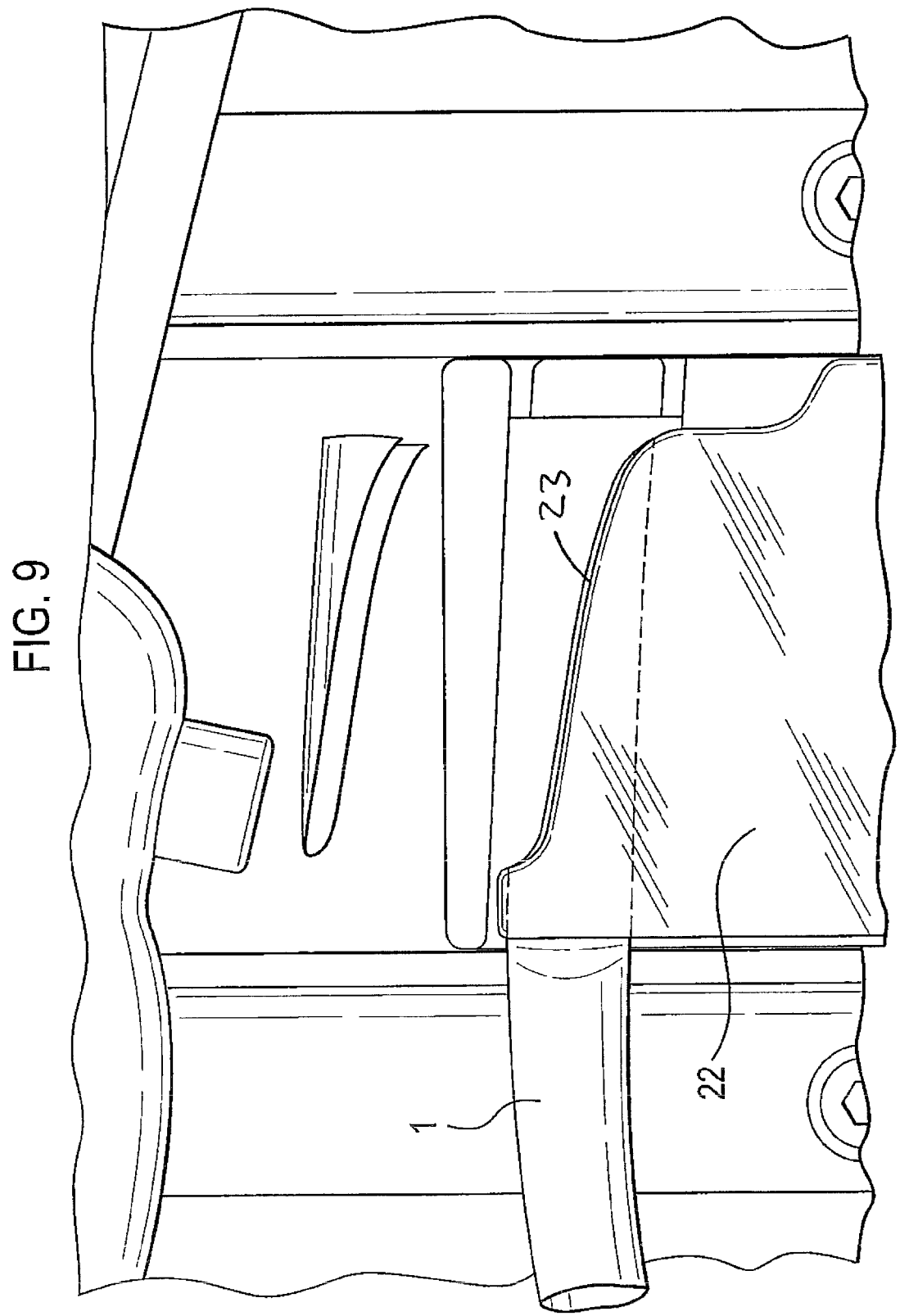
FIG. 9 is a close-up photograph, from above, of the embodiments shown in FIG. 7, after cutting has taken place.
Figure 10:
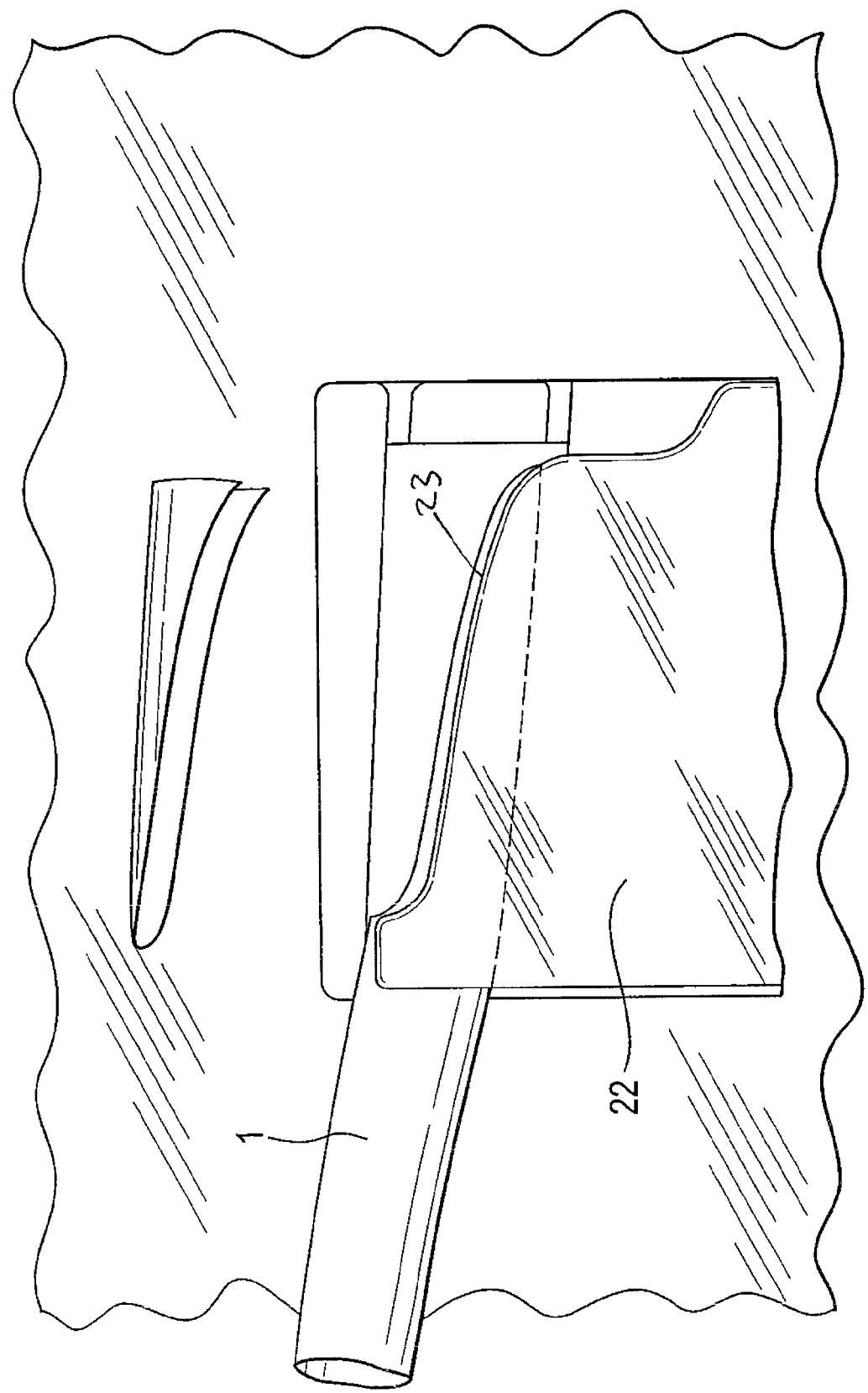
FIG. 10 is a photograph of the same subject as FIG. 9 except that the cutting press has been removed and only the template remains.

Referring to FIG. 8, the press 24 is engaged, depressing the blade, adjacent to the profiled metal template 22 so as to cut the end 19 of the tubular graft 1. When the blade is lifted, the end 19 of the tubular graft 1 is cut in the required shape as shown in FIGS. 9 to 12.

As PTFE, including ePTFE, is difficult to cut accurately, the provision of the profiled metal template 22 holds the tubular graft 1 in place as the blade cuts the tubular graft 1 to shape. The press 24 is robustly made to avoid any drifting of the blade as it shears through the tubular graft 1.

In some alternative embodiments of the invention, the internal helical ridge is replaced with another type of helical formation, such as a groove, which is capable of imparting helical flow on fluid, such as blood, passing through the tubular graft 6.

In some further embodiments of the invention, the first end 3 of the tubular graft 1 is tapered linearly from the inner base 4 to the outer tip 5. Thus, in these embodiments the orifice that forms the first end 3 of the tubular graft 1 is elliptical.

Experimental

A pre-clinical study for the Acute Assessment of an ePTFE Spiral Graft-Inline Model in accordance with one embodiment of the present invention was carried out. In particular, each of the tested grafts had profiled distal ends having an internal helical formation set at a helix angle of 17° terminating at the base of the distal end (see FIG. 13). This study was conducted over a 14 day period. The study objective was to determine that the ePTFE graft performed as intended (i.e. restores spiral laminar blood flow post surgery and pre explant).

The end-points of the study were:
1) Graft patency.
2) Presence of spiral flow in the distal graft and evaluation of flow rates.

Figure 13:
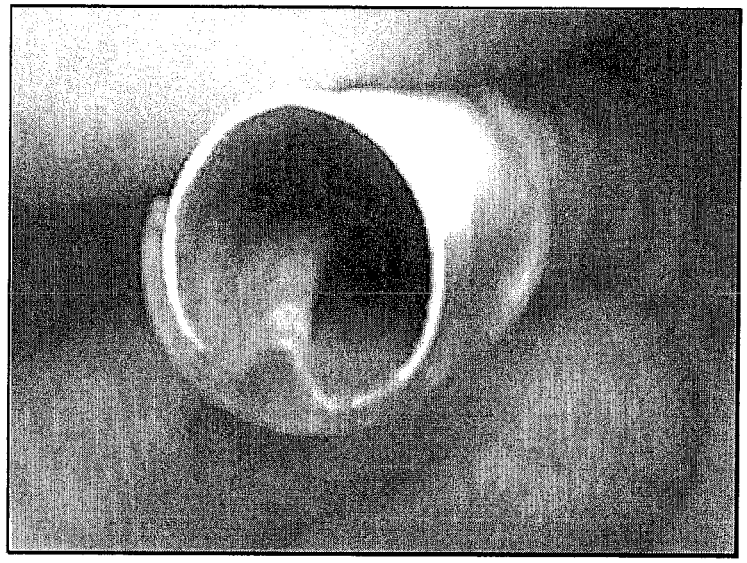
FIG. 13 is a photograph of a graft, according to one embodiment of the present invention, having a p3 Profile, and being made from ePTFE.
Figure 14:
FIG. 14 is a photograph of the internal carbon coating of the graft shown in FIG. 13, at 60× magnification.
Figure 15:
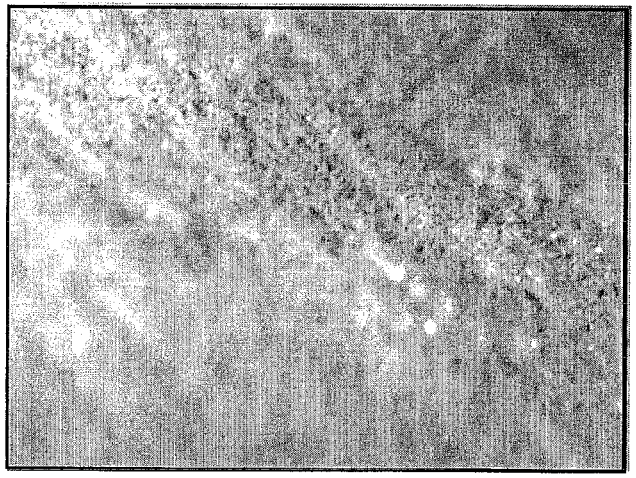
FIG. 15 is a photograph of the internal helical ridge of the stent shown in FIG. 13, at 100× magnification.

The graft used in the study is shown in FIGS. 13 to 15.

Surgical Details

Details of the animals selected for the study are shown below.

| Animal 1 (21409) | Animal 2 (21371) |
| --- | --- |
| Vessel diameter (aorta) 7 mm | Vessel diameter (aorta) 7.3 mm |
| Pulse Pre-op 82 b/min | Pulse Pre-op 118 |
| Pulse Post-op 83 b/min | Pulse Post-op 138* |
| Graft length 9.5 cm | Graft length 9 cm |
| Clamp time 30 minutes | Clamp time >40 minutes |
| No sealant required | No sealant required |
| Animal recovered well | Animal suffered Tachycardia |

Figure 16:
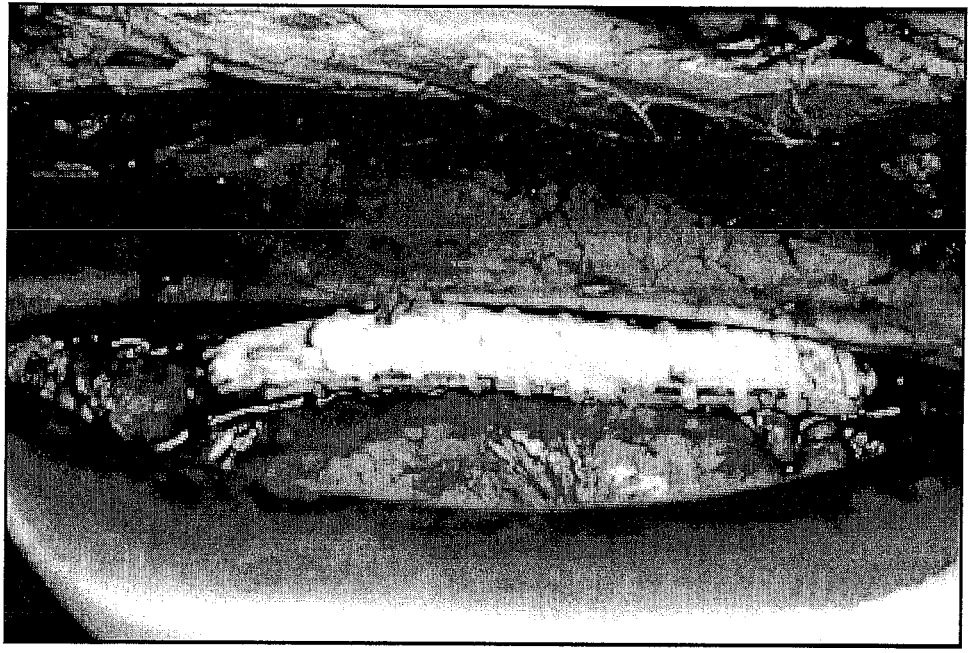
FIG. 16 is a photograph of the implant in a first sheep (21409)
Figure 17:
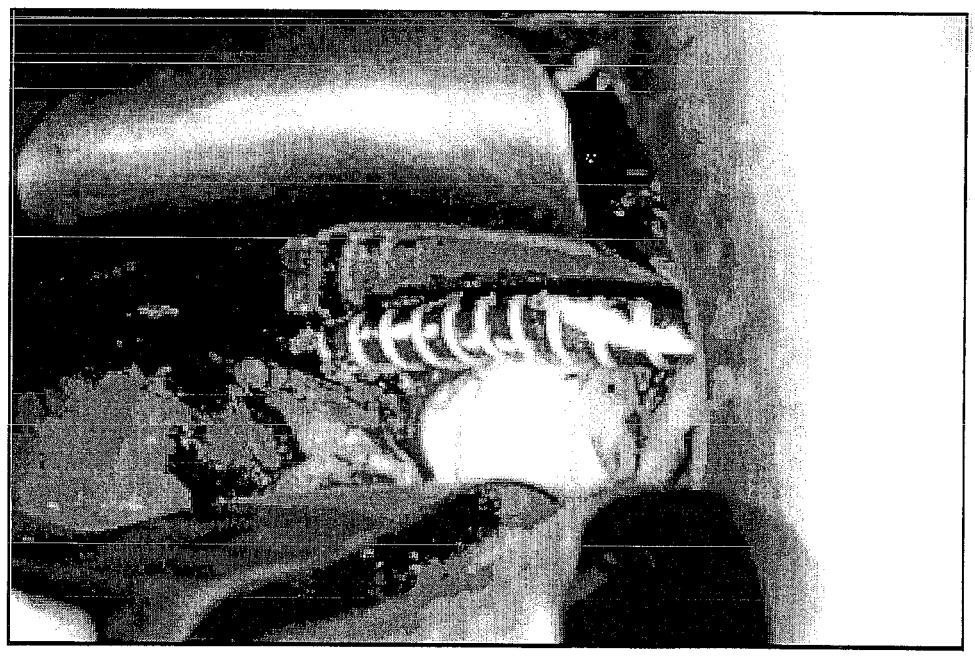
FIG. 17 is a photograph of the implant in a second sheep (21371)

The increase in pulse was considered by the veterinary surgeon to be a common effect of the medication administered to the animal.
Photographs of the implanted grafts are shown in FIGS. 16 and 17.

Surgical Conclusions

This surgical technique was performed in under one hour, and progressed as predicted and without complication. Both animals recovered quickly, and indeed progressed for 14 days prior to euthanasia without problem.

Ultrasound Results

Figure 18A:
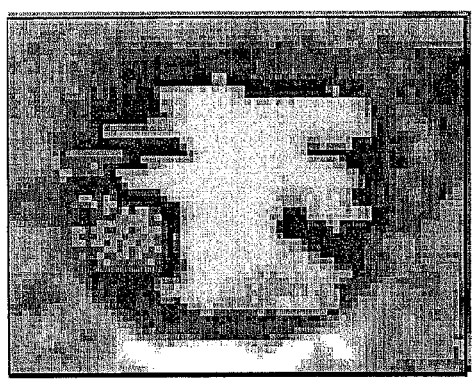
FIG. 18 is ultrasound depictions of the native aorta of the first sheep before implant (a) and after implant (b) of a graft as shown in FIG. 13 in a distal to distal anastomosis.
Figure 18B:
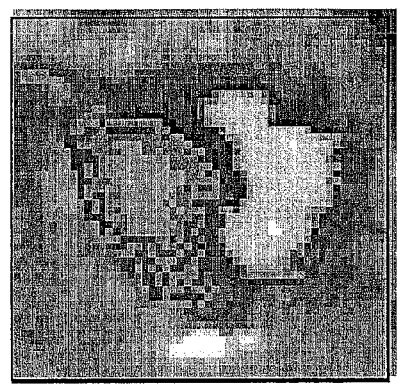
Figure 19A:
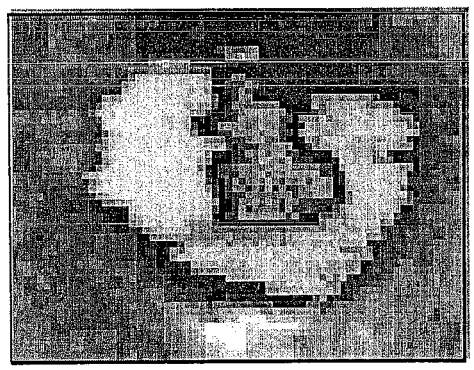
FIG. 19 is ultrasound depictions of the native aorta of the second sheep before implant (a) and after implant (b) of a graft as shown in FIG. 13 in a distal to distal anastomosis.
Figure 19B:
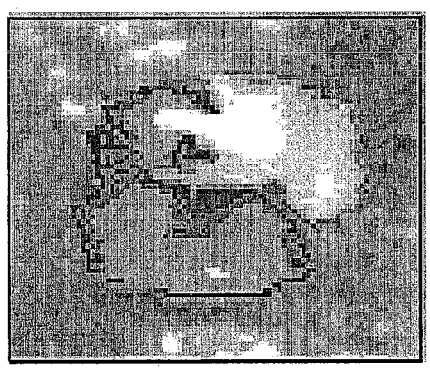

The ultrasound data for both sheep, captured at implant, is shown in FIGS. 18 and 19 and is detailed below.

The ultrasound results show that in both animals CTFS was present only after ePTFE spiral graft implantation.

TABLE 1

Animal 1 Doppler Measurements

| Pre-Implant | | Post-Implant | |
| --- | --- | --- | --- |
| Peak Systolic Approx | Peak Diastolic Approx | Peak Systolic Approx | Peak Diastolic Approx |
| | | 78.4 cm/s | 21.8 cm/s |

TABLE 2

Animal 2 Doppler Measurements

| Pre-Implant | | Post-Implant | |
| --- | --- | --- | --- |
| Peak Systolic Approx | Peak Diastolic Approx | Peak Systolic Approx | Peak Diastolic Approx |
| 112 cm/s | 33.3 cm/s | 67.7 cm/s | 31.9 cm/s |

NB the reduction in peak systolic velocity post implant (Sheep was tachycardic) was, in the opinion of the veterinary surgeon, due to the medication administered to the sheep during surgery.

Ultrasound Conclusions

Both animals did not demonstrate CTFS prior to surgery. After implantation of TFT ePTFE 170 helix ePTFE grafts, CTFS, indicating spiral flow, was clearly visible and was captured on ultrasound assessment.

Angiography at Explant

Figure 20:
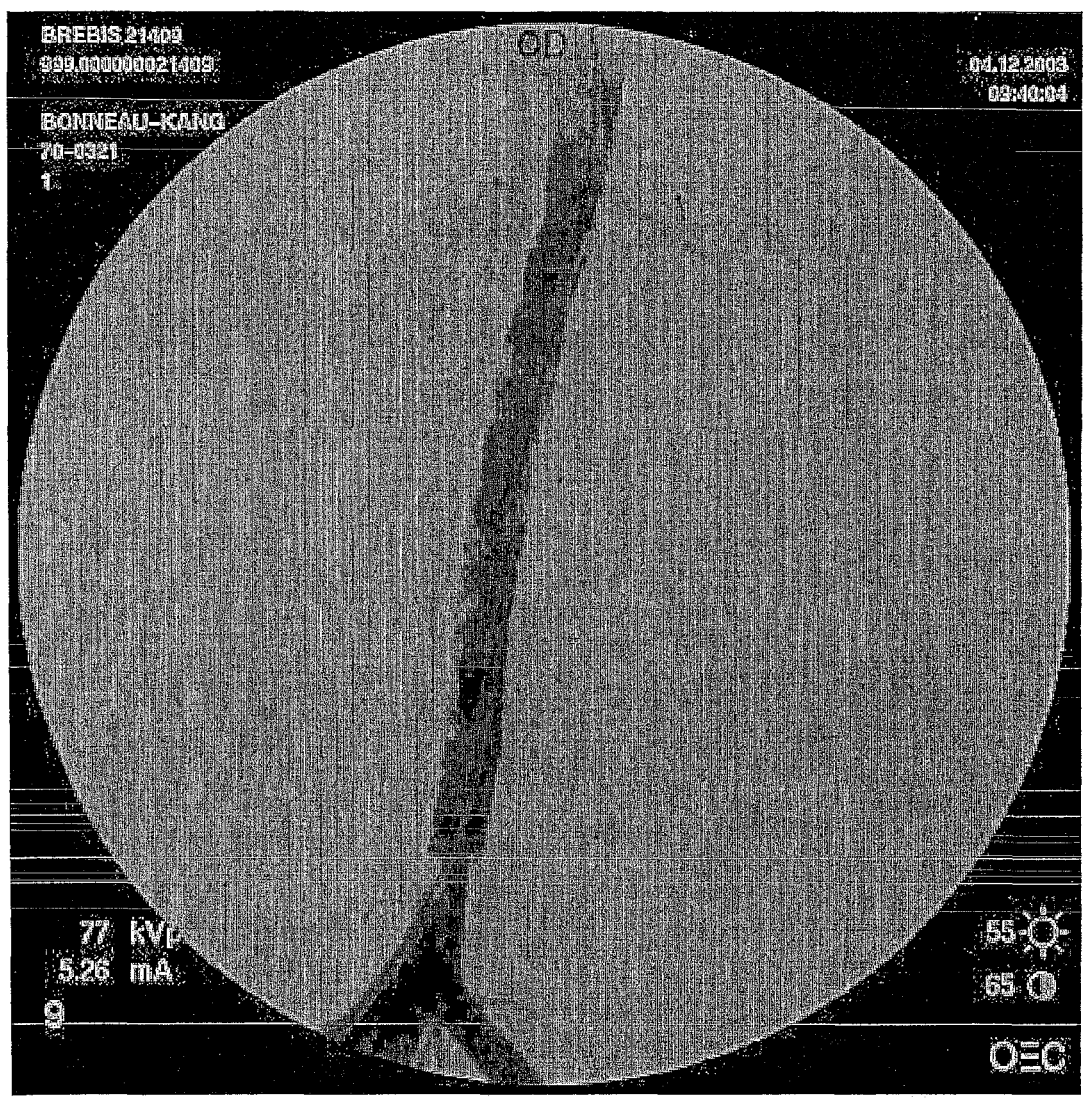
FIG. 20 is an angiograph of the first sheep at explant of the graft.
Figure 21:
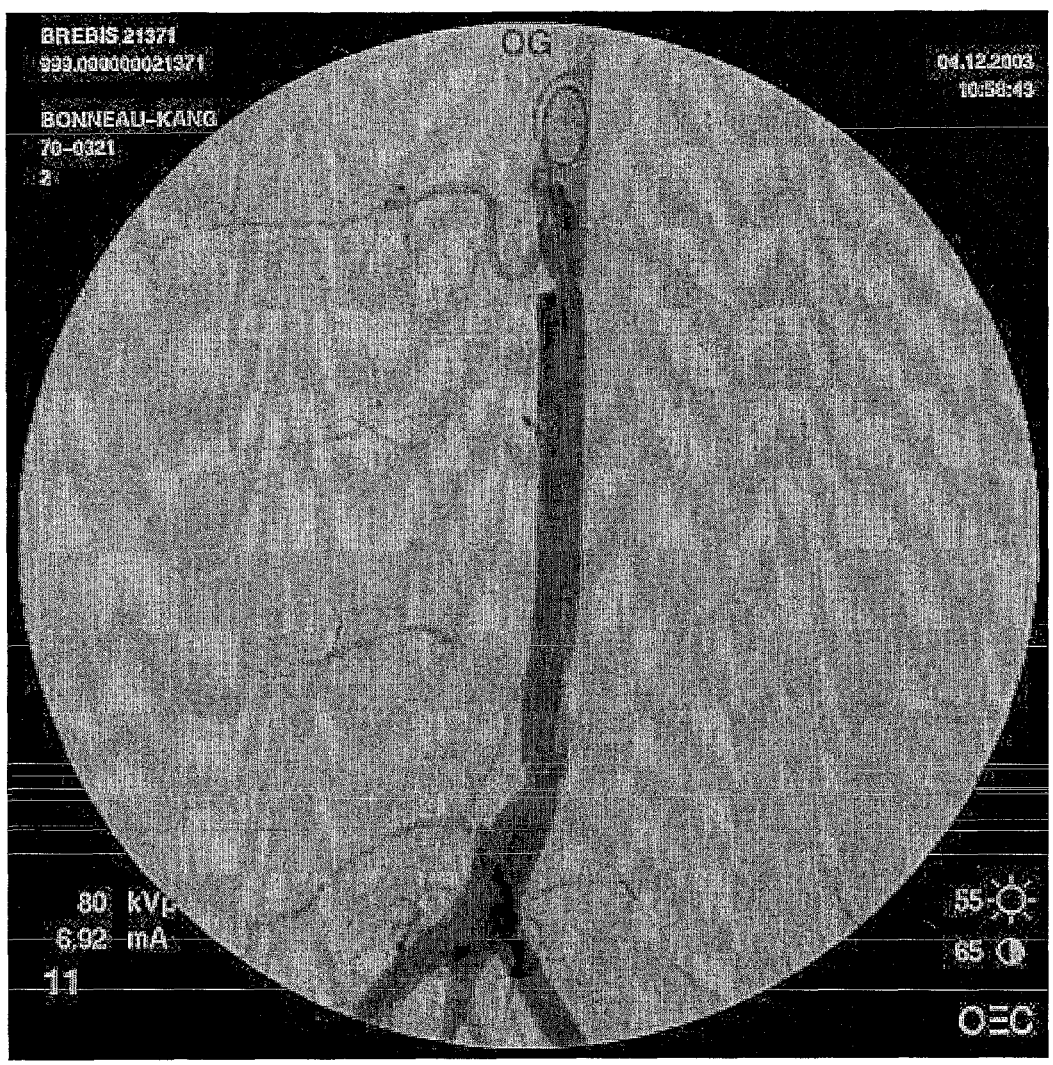
FIG. 21 is an angiograph of the second sheep at explant of the graft.

Angiograms of each animal are shown in FIGS. 20 (animal 21409) and 21 (animal 21371). Angiograms of both animals show widely patent grafts, with no stenosis at proximal or distal anastomosis.

Explants (14 Days Post Implantation)

The grafts were explanted after 14 days implantation. Photographs of the explanted grafts are shown in FIGS. 22 (animal 21409) and 23 (animal 21371). Photographs of the internal aspects of the explanted grafts are shown in FIGS. 24 (animal 21409) and 25 (animal 21371).

Figure 24:
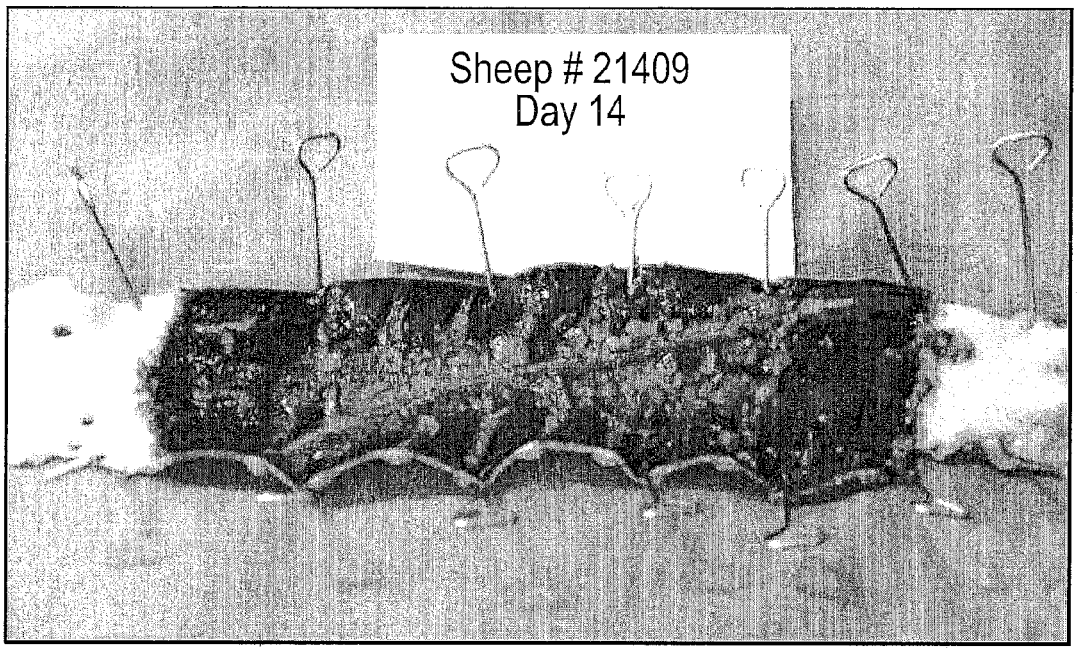
FIG. 24 is a photograph of the internal aspect of the explanted graft of the first sheep.
Figure 25:
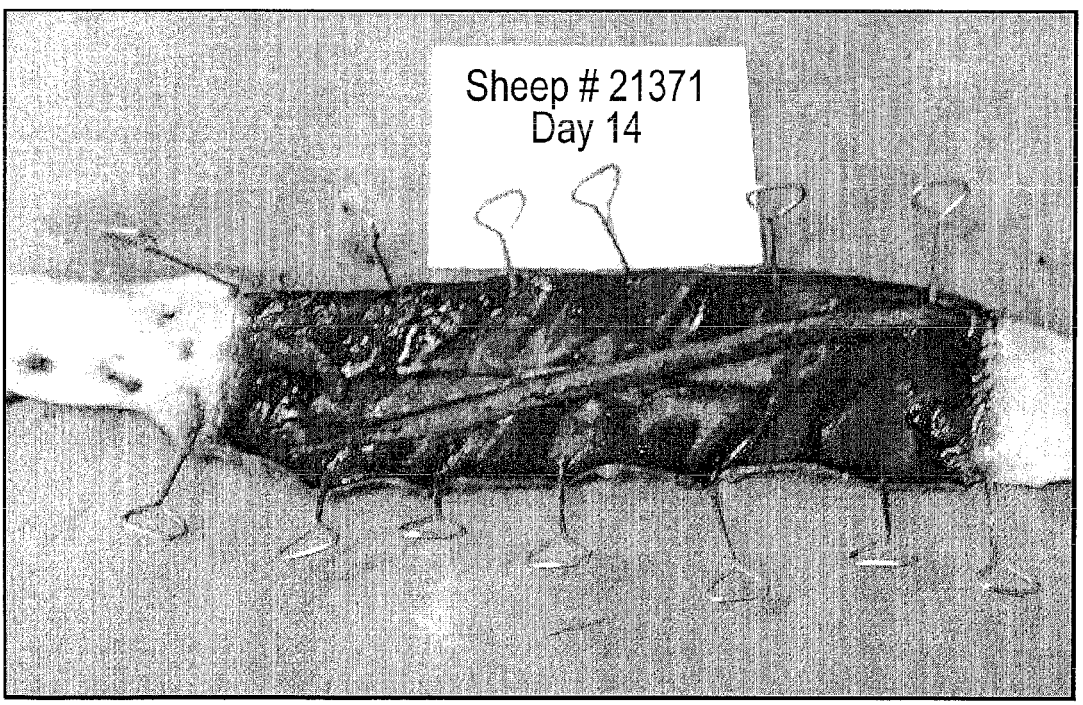
FIG. 25 is a photograph of the internal aspect of the explanted graft of the second sheep.

FIG. 24 shows that thrombus tissues were present on the internal aspect of this graft.

The explants clearly show two patent grafts after 14 days implantation.

Conclusions

The primary objectives of this study were:
1) Graft patency.
2) Presence of spiral flow in the distal graft and evaluation of flow rates.

All data collected confirmed that the primary objectives of this experiment were successfully met.

What is claimed is:

1. A tubular graft comprising:
   a tubular section defining an interior and having an internal surface, a first end defining a first orifice and a second end defining a second orifice, each of the first and second orifices leading to the interior of the tubular section; and
   an internal helical formation for imparting a helical flow on fluid passing through the tubular graft, wherein (i) the first end of the tubular graft is tapered such that the first orifice defined by the first end has an inner base and an outer tip, (ii) the internal helical formation terminates at the first orifice within a 180° arc centered on the inner base of the first orifice, and (iii) the tubular graft comprises only one internal helical formation that terminates at the first orifice, and (iv) the helix angle of the internal helical formation is between 8° and 20°.

2. The tubular graft of claim 1 wherein the first end of the tubular graft is tapered sinusoidally such that the first orifice is egg-shaped, the radius of curvature at the outer tip being smaller than the radius of curvature at the inner base.

3. The tubular graft of claim 1 wherein the internal helical formation terminates at the first orifice within a 120° arc centered on the inner base.

4. The tubular graft of claim 1 wherein the internal helical formation terminates at the first orifice within a 60° arc centered on the inner base.

5. The tubular graft of claim 1 wherein the internal helical formation terminates at the first orifice at the inner base.

6. The tubular graft of claim 1 wherein the internal helical formation is a ridge which extends inwardly from the internal surface of the tubular graft.

7. The tubular graft of claim 1 further comprising an external helical formation for supporting the tubular graft.

8. The tubular graft of claim 7 wherein the external helical formation has a helix angle greater than 50°.

9. The tubular graft of claim 7 wherein the external helical formation has a helix angle between 65° and 80°.

10. The tubular graft of claim 1 wherein the second end of the tubular graft is tapered in the same way as the first end.

* * * * *